United States Patent
Park et al.

(10) Patent No.: US 10,824,908 B1
(45) Date of Patent: Nov. 3, 2020

(54) APPARATUS FOR PREDICTING METADATA OF MEDICAL IMAGE AND METHOD THEREOF

(71) Applicant: Lunit Inc., Seoul (KR)

(72) Inventors: Jongchan Park, Seoul (KR); Donggeun Yoo, Seoul (KR)

(73) Assignee: Lunit Inc., Seoul (KR)

( * ) Notice: Subject to any disclaimer, the term of this patent is extended or adjusted under 35 U.S.C. 154(b) by 0 days.

(21) Appl. No.: 16/708,205

(22) Filed: Dec. 9, 2019

(30) Foreign Application Priority Data

May 22, 2019 (KR) .......................... 10-2019-0059860

(51) Int. Cl.
*G16H 30/20* (2018.01)
*G06K 9/62* (2006.01)
(Continued)

(52) U.S. Cl.
CPC .......... *G06K 9/6256* (2013.01); *G06T 7/0012* (2013.01); *G06T 7/70* (2017.01);
(Continued)

(58) Field of Classification Search
CPC .......... G06N 20/00; G06N 3/02; G06N 7/005; G06N 5/046; G06N 3/08; G06N 5/047; G06N 20/20; G06N 3/0454; G16H 30/20; G16H 50/20; G16H 30/40; G06T 7/0012; G06T 2207/10116; G06T 2207/20081; G06T 2207/30004; G06T 2207/10081;
(Continued)

(56) References Cited

U.S. PATENT DOCUMENTS 10,222,942 B1 * 3/2019 Zeiler ...................... G06F 40/30
2019/0057501 A1 * 2/2019 Lo ........................... A61B 5/055
(Continued)

FOREIGN PATENT DOCUMENTS

JP 2013-182444 A 9/2013
KR 10-2013-0022474 A 3/2013
(Continued)

OTHER PUBLICATIONS

Philbrick et al., RIL-Contour: a Medical Imaging Dataset Annotation Tool for and with Deep Learning, Journal of Digital Imaging, May 14, 2019 [retrieved Mar. 6, 2020], 32, 571-581. Retrieved: https://link.springer.com/article/10.1007/s10278-019-00232-0 (Year: 2019).*

(Continued)

*Primary Examiner* — Andrew M Moyer
*Assistant Examiner* — Dennis Rosario
(74) *Attorney, Agent, or Firm* — Knobbe Martens Olson & Bear LLP

(57) ABSTRACT

This disclosure relates to a computerized method to perform a machine learning on a relationship between medical images and metadata using a neural network and acquiring metadata by applying a machine learning model to medical images, and a method thereof. The apparatus and method may include training a prediction model for predicting metadata of medical images based on multiple medical images for learning and metadata matched with each of multiple medical images and predicting metadata of input medical image.

20 Claims, 10 Drawing Sheets

(51) Int. Cl.
  *G06T 7/00*  (2017.01)
  *G06T 7/70*  (2017.01)
(52) U.S. Cl.
  CPC ... *G16H 30/20* (2018.01); *G06T 2207/20081* (2013.01); *G06T 2207/20084* (2013.01); *G06T 2207/30004* (2013.01)
(58) Field of Classification Search
  CPC . G06T 2207/10088; G06T 2207/10132; G06T 2207/30061; G06T 2207/20084; G06K 2209/05; G06K 9/6256; G06K 9/6262; G06K 9/66; A61B 6/032; A61B 6/563; A61B 5/055; A61B 5/7264
  See application file for complete search history.

(56) References Cited

U.S. PATENT DOCUMENTS

| | | | |
|---|---|---|---|
| 2019/0279082 A1* | 9/2019 | Moloney | G06K 9/4628 |
| 2019/0392547 A1* | 12/2019 | Katouzian | G06N 20/00 |

FOREIGN PATENT DOCUMENTS

| | | |
|---|---|---|
| KR | 10-2018-0040287 A | 4/2018 |
| KR | 10-2018-0061698 A | 6/2018 |

OTHER PUBLICATIONS

Qayyum et al., Medical image retrieval using deep convolutional neural network, Nov. 29, 2017 [retrieved Mar. 6, 2020], Neurocomputing, vol. 266,pp. 8-20. Retrieved: https://www.sciencedirect.com/science/article/pii/S0925231217308445 (Year: 2017).*

Möller et al., RadSem: Semantic Annotation and Retrieval for Medical Images, 2009 [retrieved Jun. 26, 2020],The Semantic Web: Research and Applications. ESWC 2009. Lecture Notes in Computer Science, vol. 5554, pp. 21-35. Retrieved: https://link.springer.com/chapter/10.1007/978-3-642-02121-3_6#citeas (Year: 2009).*

Office Action of corresponding Korean Patent Application No. 10-2019-0059860 and its English Translation—9 pages (dated Aug. 19, 2019).

Notice of Alloance of corresponding Korean Patent Application No. 10-2019-0059860 and its English Translation—6 pages (dated Dec. 27, 2019).

* cited by examiner

APPARATUS FOR PREDICTING METADATA OF MEDICAL IMAGE AND METHOD THEREOF

CROSS-REFERENCE TO RELATED PATENT APPLICATION

This application claims the benefit of Korean Patent Application No. 10-20190059860, filed on May 22, 2019, in the Korean Intellectual Property Office, the disclosure of which is incorporated herein in its entirety by reference.

BACKGROUND

1. Technical Field

This disclosure generally relates to an apparatus for performing machine learning on relationship between a medical image and metadata using a neural network and acquiring metadata by applying a machine learning model to the medical image.

2. Discussion of Related Technology

According to digital imaging and communications and medicine (DICOM) which is a data standard for medical images, DICOM data largely contain two types of information. One is an original medical image taken (raw pixel array), and the other is metadata recorded on a DICOM header.

During an medical image analysis, values recorded on the DICOM header are used first. For instance, medical workers determine whether a medical image corresponds to patient's body part by looking at "BodyUnitExamined" attribute of the DICOM header before interpreting the medical image. In addition, medical workers can normalize original images that come from diverse environments using "Window Center/Width" attribute of the DICOM header.

SUMMARY

Each hospital has a different protocol for metadata of such medical images saved on the DICOM header, and a different subjective value may be entered by each radiologist. The DICOM header may not have values, have incorrect values, or have values saved according to different criteria. In this case, medical workers cannot interpret medical images or might interpret them incorrectly. In addition, normalized medical images are required to learn medical images by machine learning, but machine teaming cannot be performed properly on medical images if their metadata are saved according to different criteria.

A computerized method of analyzing medical images according to an embodiment of this disclosure comprises learning a prediction model for predicting metadata of an input medical image based on multiple medical images (training medical images) and metadata matched with each of the multiple medical images and predicting metadata of the input medical image using the learned prediction model.

The metadata in the method of analyzing medical images according to an embodiment of this disclosure comprises at least one of information related to objects included in the medical image, information (e.g., one or more parameters) about shooting environment of the medical image, and information related to display method of the medical image.

In the method of analyzing medical images according to an embodiment of this disclosure, information related to objects included in the medical images comprises at least one of information about body parts included in the medical images and information about patient, information about shooting environment of the medical images comprises at least one of modality information of medical images and information about shooting method of the medical images, and information related to display method of the medical images comprises at least one of window center information of the medical images, window width information, color inversion information, image rotation information, and image flip information.

In the method of analyzing medical images according to an embodiment of this disclosure, learning a prediction model for the medical image analysis method comprises acquiring multiple metadata that match each of multiple medical images from standard data elements of DICOM header of each of multiple medical images and learning the prediction model using multiple medical images for learning and multiple metadata acquired.

In the method of analyzing medical images according to an embodiment of this disclosure, learning a prediction model additionally comprises matching and saving metadata predicted for input medical image with the input medical image.

In the method of analyzing medical images according to an embodiment of this disclosure, saving the metadata comprises saving the predicted metadata on DICOM header of the input medical image.

The method of analyzing medical images according to an embodiment of this disclosure additionally comprises adjusting the input medical image based on the predicted metadata to detect anomaly in the input medical image.

In the method of analyzing medical images according to an embodiment of this disclosure, adjusting the input medical image comprises adjusting at least one of window center of the input medical image, window width, color, and output direction.

In the method of analyzing medical images according to an embodiment of this disclosure, the multiple medical images for learning and the input medical image are images that correspond to DICOM standard.

An apparatus for analyzing medical images according to an embodiment of this disclosure comprises a processor and memory. The processor uses instructions stored on the memory to execute training a prediction model for predicting metadata of the medical images based on multiple medical images and metadata matched with each of the multiple medical images and predicting metadata of the input medical image using the trained prediction model.

In the apparatus for analyzing medical image according to an embodiment of this disclosure, metadata includes at least one of information related to objects included in the medical image, information about shooting environment of the medical image, and information related to display method of the medical image.

In the apparatus for analyzing medical image according to an embodiment of this disclosure, information related to objects included in the medical image comprises at least one of information body parts included in the medical image and information about patient, information about shooting environment of medical image comprises at least one of modality information of the medical image and information about shooting method of the medical image, and information related to display method of the medical image comprises at least one of window center information, window width information, color inversion information, image rotation information, and image flip information of the medical image.

In the apparatus for analyzing medical image according to an embodiment of this disclosure, the processor uses instructions stored on the memory to execute acquiring multiple metadata that match each of the multiple medical images from standard data elements of DICOM header of each of the multiple medical images and training the prediction model using the multiple medical images for training and multiple metadata acquired.

In the apparatus for analyzing medical image according to an embodiment of this disclosure, the processor uses instructions stored on the memory to further execute matching and saving the metadata predicted for the input medical image with the input medical image.

In the apparatus for analyzing medical image according to an embodiment of this disclosure, the processor uses instructions stored on the memory to further execute saving the predicted metadata on DICOM header of the input medical image.

In the apparatus for analyzing medical image according to an embodiment of this disclosure, the processor uses instructions stored on the memory to further execute adjusting the input medical image based on the predicted metadata to detect anomaly in the input medical image.

In the apparatus for analyzing medical images according to an embodiment of this disclosure, the processor uses instructions stored on the memory to further execute adjusting at least one of window center, window width, color, and output direction of the input medical image based on the predicted metadata.

In the apparatus for analyzing medical image according to an embodiment of this disclosure, the multiple medical images for training and input medical image are images that correspond to the DICOM standard.

In addition, a program to embody the method of analyzing medical image can be recorded on a computer readable recording medium.

BRIEF DESCRIPTION OF THE DRAWINGS

These and/or other aspects will become apparent and more readily appreciated from the following description of embodiments, taken in conjunction with the accompanying drawings.

DETAILED DESCRIPTION

Figure 1:
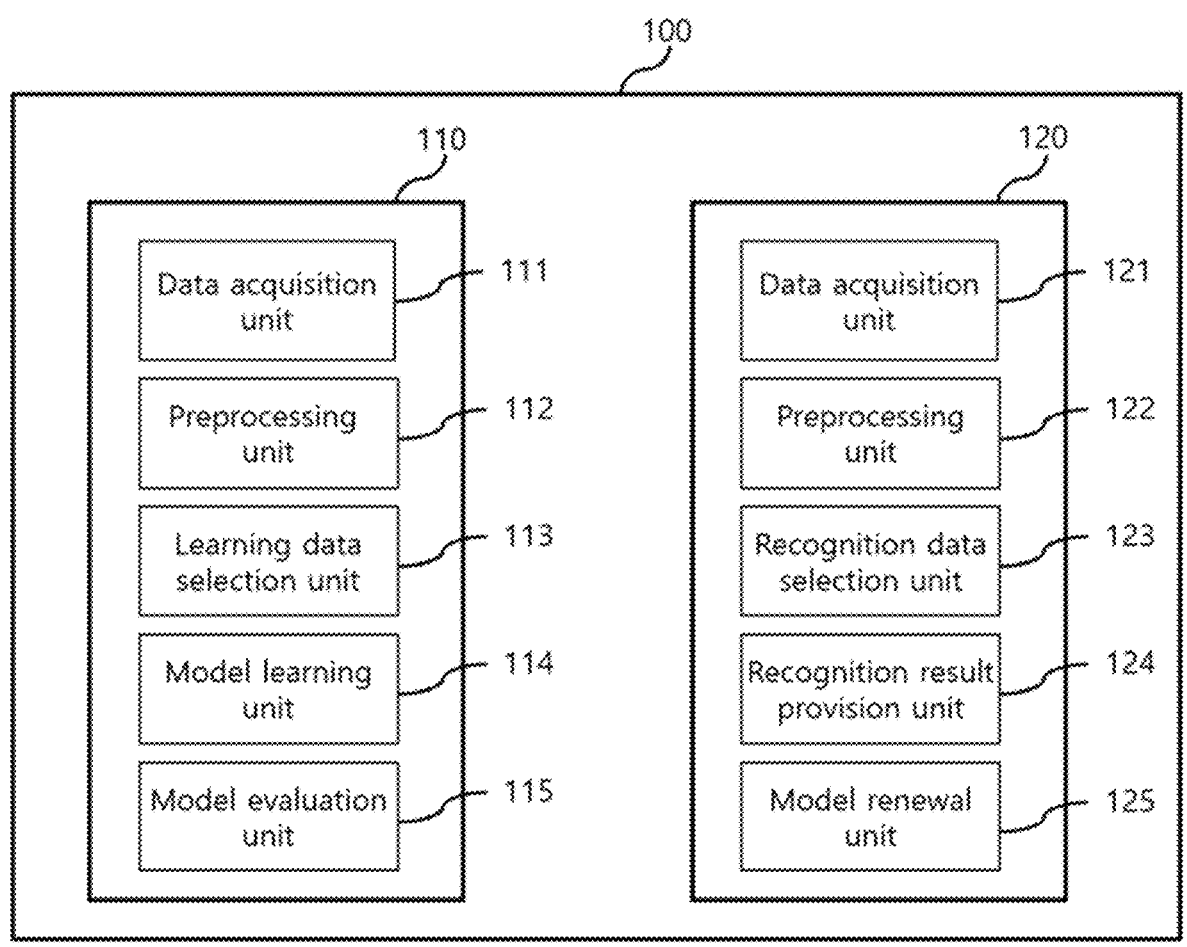
FIG. 1 is a block diagram of a medical image analysis apparatus according to an embodiment of this disclosure.

Merits and characteristics of embodiments disclosed and methods of achieving them would be clarified by referring to the embodiments described below with attached drawings. However, this disclosure is not limited to the embodiments disclosed below and can be embodied into diverse forms. These embodiments are simply provided to make this disclosure complete and to completely inform the scope of this invention to persons with common knowledge in the technical field of this disclosure.

Terms used in this specification will be explained briefly. The terms used in this specification are ordinary terms that are used widely, selected in consideration of functions of this disclosure. These terms can change according to intention of engineers who work in related fields, precedents, appearance of new technologies, etc. In addition, certain terms were selected arbitrarily by the applicant, for which case meanings of such terms will be explained in detail. Therefore, the terms used in this disclosure must be defined based on their definitions and overall application in this disclosure instead of their names.

Unless clearly specified to be singular, singular expressions used in this specification shall also include plurality. In addition, unless clearly specified to be plural, plural expressions shall include singularity.

When a part of this specification is said to "comprise" a component, this does not exclude other components and means that other components can also be included unless specifically described otherwise.

In addition, term "unit" used in this specification refers to a software or hardware component. A "unit" plays certain roles, but it is not limited to software or hardware. A "unit" can exist in an addressable storage medium or play one or more processors. Therefore, for instance, "units" include components such as software components, object-oriented software components, class components and task components, processes, functions, attributes, procedures, subroutines, program code segments, drivers, firmware, microcode, circuit, data, database, data structures, tables, arrays, and variables. Functions provided within components and "units" can be combined into smaller number of components and "units" or subdivided into additional components and "units."

According to an embodiment of this disclosure, "units" can be embodied using a processor and a memory. The term "processor" is interpreted broadly to include a general-purpose processor, a central processing unit (CPU), a microprocessor, a digital signal processor (DSP), a controller, a microcontroller, a state machine, etc. In some environments, "processor" may refer to application specific integrated circuit (ASIC), programmable logic device (PLD), field programmable gate array (FPGA), etc. The term "processor" may, for instance, also refer to combination of a DSP and a microprocessor, a combination of multiple microprocessors, a combination of one or more microprocessors combined with a DSP core, or combination of processing devices that is same as other combinations of such configuration.

The term "memory" is interpreted broadly to include a random electronic component that can save electronic information. The term memory may also refer to various types of processor-readable medium such as random-access memory (RAM), read-only memory (ROM), non-volatile random-access memory (NVRAM), programmable read-only memory (PROM), erasable programmable read-only memory (EPROM), electrically erasable pROM (EEPROM), flash memory, magnetic or optical data storage device, registers, etc. Whereas a processor can read information from a memory and record information on a memory, a memory is called to be in electronic communication with a processor. A memory integrated with a processor is in electronic communication with the processor.

Certain embodiments of the present disclosure are explained in detail below by referring to attached figures so that this disclosure can be easily implemented by persons with common knowledge in the technical field of this disclosure. To clarify explanation of this disclosure in the figures, parts irrelevant to the explanation are omitted.

FIG. 1 is a block diagram of a medical image analysis apparatus (100) according to an embodiment of this disclosure.

Referring to FIG. 1, the medical image analysis device (100) according to an embodiment can comprise a data learning unit (110) and a data recognition unit (120). The medical image analysis device (100) can comprise a processor and memory.

The data learning unit (110) can learn a machine learning model using a data set to perform a target task. The data learning unit (110) can receive label information related to the data set and target task. The data learning unit (110) can acquire the machine learning model by performing machine learning on a relationship between the data set and label information. The machine learning model acquired by the data learning unit (110) can be a model to generate the label information using the data set.

The data recognition unit (120) can receive and save the machine learning model of the data learning unit (110). The data recognition unit (120) can output the label information by applying input data to the machine learning model. In addition, the data recognition unit (120) can be used to renew the machine learning model using the input data, label information, and output from the machine learning model.

At least one of the data learning unit (110) and data recognition unit (120) can be made into at least one hardware chip and mounted on electronic apparatus. For instance, at least one of the data learning unit (110) and data recognition unit (120) can be made into an exclusive hardware chip for artificial intelligence (AI) or as a unit of an existing general-purpose processor (e.g. CPU or application processor) or graphic-only processor (e.g. GPU) to be mounted on various electronic apparatus explained earlier.

In addition, the data learning unit (110) and data recognition unit (120) can be mounted separately on different electronic apparatuses. For instance, one of the data learning unit (110) and the data recognition unit (120) can be included in an electronic apparatus with the other one included in a server. In addition, the data learning unit (110) and data recognition unit (120) can be connected with or without wire to provide the machine learning model constructed by the data learning unit (110) to the data recognition unit (120) or provide the input data of the data recognition unit (120) to the data learning unit (110) as additional learning data.

On the one hand, at least one of the data learning unit (110) and data recognition unit (120) can be embodied into a software module. If at least one of the data learning unit (110) and data recognition unit (120) is embodied into a software module (or a program module that includes instructions), the software module can be saved on the memory or non-transitory computer readable media. In addition, in this case, at least one software module can be provided by an operating system (OS) or by a prescribed application. Otherwise, at least one software module can have a portion provided by an OS and the other portion provided by a prescribed application.

The data learning unit (110) according to an embodiment of this disclosure can include a data acquisition unit (111), a preprocessing unit (112), a learning data selection unit (113), a model learning unit (114), and a model evaluation unit (115).

The data acquisition unit (111) can acquire data necessary for machine learning. Since a large volume of data is needed for learning, the data acquisition unit (111) can receive data sets that include multiple data.

The label information can be assigned to each of multiple data. The label information may be information that explains each of multiple data. The label information may be information to be derived by the target task. The label information can be acquired from user input, memory, or result of the machine learning model. For instance, if the target task is to determine existence of a certain object in an image, multiple data would be multiple image data and the label information would be whether the certain object exists in each of multiple images.

The preprocessing unit (112) can preprocess acquired data so that data received can be used for machine learning. The preprocessing unit (112) can process the acquired data sets into a preset format to be used by the model learning unit (114) to be described later.

The learning data selection unit (113) can select data necessary for learning among preprocessed data. Selected data can be provided to the model learning unit (114). The learning data selection unit (113) can select data necessary for learning among preprocessed data according to the preset standards. In addition, the learning data selection unit (113) can also select data according to the preset standards through learning of the model learning unit (114) to be described later.

The model learning unit (114) can learn standards for label information output based on the data set. In addition, the model learning unit (114) can perform machine learning by using the data set and label information of the data set as learning data. In addition, the model learning unit (114) can perform machine learning by additionally using the acquired machine learning model. In this case, the acquired machine learning model can be a model constructed in advance. For instance, the machine learning model can be a model constructed in advance by receiving default learning data.

The machine learning model can be constructed by considering application field of the learning model, purpose of learning, computer performance of the apparatus, etc. The machine learning model, for instance, can be a model based on a neural network. For example, models like deep neural network (DNN), recurrent neural network (RNN), long short-term memory models (LSTM), bidirectional recurrent deep neural network (BRDNN), and convolutional neural networks (CNN) can be used as machine learning models, but the machine learning model is not limited to them.

According to various embodiments, if there are multiple machine learning models constructed in advance, the model learning unit (114) can decide a machine learning model that is highly associated with input learning data and default learning data as the machine learning model to be learned. In this case, default learning data can be already classified into data types, and the machine learning model can be constructed in advance for each data type. For instance, default learning data can be classified in advance according to various criteria including place where learning data are generated, time at which learning data are generated, size of learning data, a learning data generator, an object type of learning data, etc.

In addition, the model learning unit (114), for instance, can learn the machine learning model using a teaming algorithm that includes error back-propagation or gradient descent.

In addition, the model learning unit (114), for instance, can learn the machine learning model through supervised learning that uses learning data as input values. In addition, the model learning unit (114), for instance, can acquire the machine learning model through unsupervised learning that finds criteria for the target task by learning a data type needed for the target task on its own without supervision. In addition, the model learning unit (114), for instance, can learn the machine learning model through reinforcement learning that uses feedback on correctness of the result of the target task according to learning.

In addition, once the machine learning model is teamed, the model learning unit (114) can save the learned machine learning model. In this case, the model learning unit (114) can save the learned machine learning model on the memory of electronic apparatus that includes the data recognition unit (120). Otherwise, the model learning unit (114) can also save the learned machine learning model on the memory of the server connected to the electronic apparatus connected via wired or wireless network.

The memory that saves the learned machine learning model, for instance, can also save commands or data related to at least one other component of electronic apparatus. In addition, the memory can save software and/or programs. Programs, for instance, may comprise kernel, middleware, application programming interface (API) and/or application program (or "application"), etc.

The model evaluation unit (115) can enter evaluation data into the machine teaming model and make the model learning unit (114) repeat learning if the output results from evaluation data fail to satisfy prescribed criteria. In this case, evaluation data may be preset data to evaluate the machine learning model.

For instance, in the results of the machine learning model learned for evaluation data, the model evaluation unit (115) can be evaluated as to not satisfy the prescribed criteria if the number or ratio of evaluation data with inaccurate recognition result exceeds the preset threshold value. For example, if the prescribed criteria are defined as ratio of 2% and the learned machine learning model outputs incorrect recognition result for 20 evaluation data out of 1,000 evaluation data, the model evaluation unit (115) can evaluate that the learned machine learning model is inappropriate.

On the one hand, if there are multiple learned machine learning models, the model evaluation unit (115) can evaluate whether each of the image learning model satisfies the prescribed criteria and decide the model that satisfies the prescribed criteria as the final machine learning model. In this case, if multiple models satisfy the prescribed criteria, the model evaluation unit (115) can decide one or prescribed number of models preset according to evaluation score as the final machine learning model.

On the one hand, at least one of the data acquisition unit (111), the preprocessing unit (112), the learning data selection unit (113), the model learning unit (114), and the model evaluation unit (115) in the data learning unit (110) can be made into at least one hardware chip and mounted on the electronic apparatus. For instance, at least one of the units 111-115 can be made into an exclusive hardware chip for artificial intelligence (AI) or be made into a unit of an existing general-purpose processor (e.g. CPU or application processor) or graphic-only processor (e.g. GPU) and mounted on various electronic apparatus described earlier.

In addition, the data acquisition unit (111), the preprocessing unit (112), the learning data selection unit (113), the model learning unit (114), and the model evaluation unit (115) may be mounted on an electronic apparatus or separately on different electronic apparatuses. For instance, the units 111-115 may have some of them included in the electronic apparatus and others in the server.

In addition, at least one of the units 111-115 can be embodied into a software module. If at least one of the data acquisition unit (111), the preprocessing unit (112), the learning data selection unit (113), the model learning unit (114), and the model evaluation unit (115) is embodied into a software module (or a program module that includes instructions), the software module can be saved on non-transitory computer readable media. In addition, in this case, at least one software module can be provided by an OS or by a prescribed application. Otherwise, at least one software module can have a portion provided by an OS and the other portion provided by a prescribed application.

The data recognition unit (120) according to an embodiment of this disclosure may include a data acquisition unit (121), a preprocessing unit (122), a recognition data selection unit (123), a recognition result provision unit (124), and a model renewal unit (125).

The data acquisition unit (121) can receive input data. The preprocessing unit (122) can preprocess input data acquired so that input data acquired is used by the recognition data selection unit (123) or recognition result provision unit (124).

The recognition data selection unit (123) can select necessary data among preprocessed data. Selected data can be provided to the recognition result provision unit (124). The recognition data selection unit (123) can select a unit or all of preprocessed data according to preset criteria. In addition, the recognition data selection unit (123) can also select data according to the preset criteria through learning by the model learning unit (114).

The recognition result provision unit (124) can acquire result data by applying selected data to the machine learning model. The machine learning model can be a machine learning model generated by the mode learning unit (114). The recognition result provision unit (124) can output result data.

The model renewal unit (125) can renew the machine learning model based on evaluation of a recognition result provided by the recognition result provision unit (124). For instance, the model renewal unit (125) can make the model learning unit (114) renew the machine learning model by providing a recognition result provided by the recognition result provision unit (124) to the model learning unit (114).

On the one hand, at least one of the data acquisition unit (121), the preprocessing unit (122), the recognition data selection unit (123), the recognition result provision unit (124), and the model renewal unit (125) in the data recognition unit (120) can be made into at least one hardware chip and mounted on the electronic apparatus. For instance, at least one of the units 121-125 can be made into an exclusive hardware chip for artificial intelligence (AI) or made into a unit of an existing general-purpose processor (e.g. CPU or application processor) or graphic-only processor (e.g. GPU) and mounted on various electronic apparatus described earlier.

In addition, the units 121-125 can be mounted on one electronic apparatus or separately on different electronic apparatuses. For instance, the data acquisition unit (121), the preprocessing unit (122), the recognition data selection unit (123), the recognition result provision unit (124), and the model renewal unit (125) can have some of them included in the electronic apparatus and others in the server.

In addition, at least one of the units 121-125 can be embodied into a software module. If at least one of these units 121-125 is embodied into a software module (or a program module that includes instructions), the software module can be saved on a non-transitory computer readable media. In addition, in this case, at least one software module can be provided by an OS or by a prescribed application. Otherwise, at least one software module can have a portion provided by an OS and the other portion provided by a prescribed application.

Method of sequential machine learning of data sets by the data learning unit (110) and apparatus thereof are explained in greater detail below.

Figure 2:
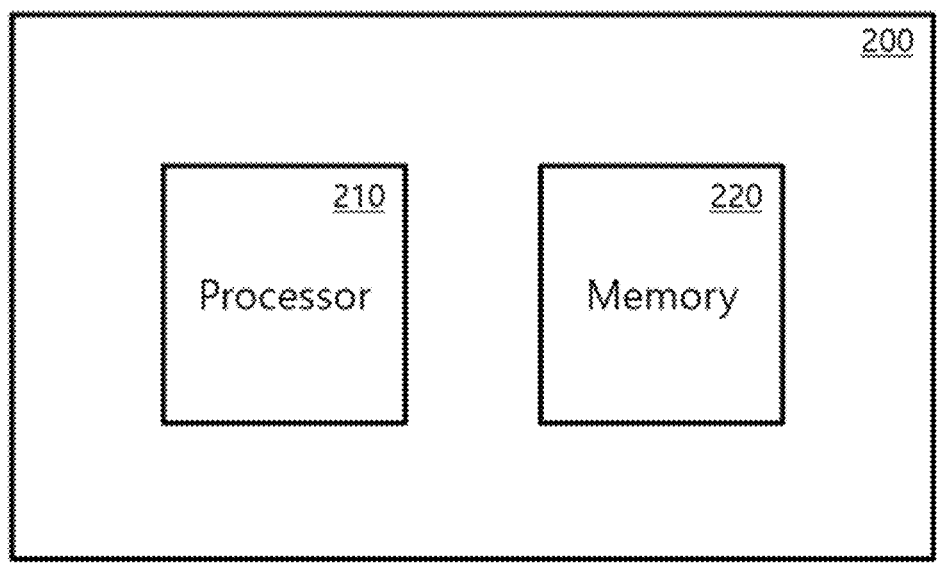
FIG. 2 is a figure that represents the medical image analysis apparatus according to an embodiment of this disclosure.

FIG. 2 is a figure that represents the medical image analysis apparatus according to an embodiment of this disclosure.

The medical image analysis apparatus (200) can include a processor (210) and a memory (220). The processor (210) can execute instructions stored on the memory (220).

As described above, the medical image analysis apparatus (200) can comprise at least one of a data learning unit (110) and a data recognition unit (120). At least one of the data learning unit (110) and data recognition unit (120) can be embodied by the processor (210) and memory (220).

An operation of the medical image analysis device (200) is explained in greater detail below.

Figure 3:
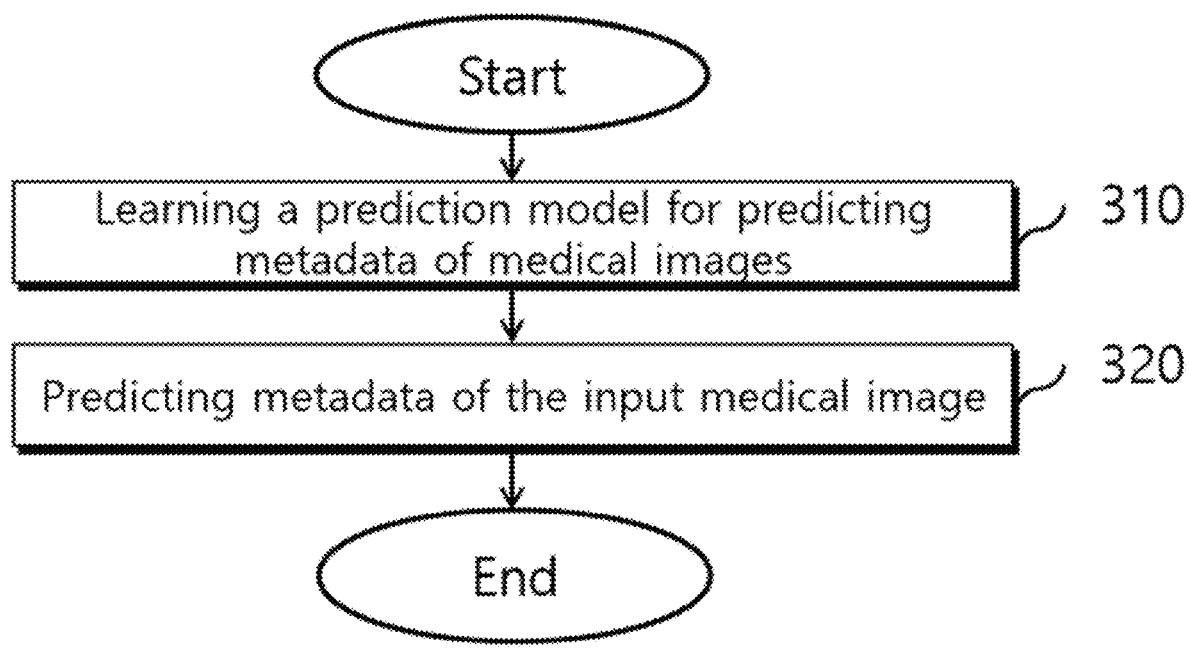
FIG. 3 is a flow diagram that illustrates operation of the medical image analysis apparatus according to an embodiment of this disclosure.

FIG. 3 is a flow diagram that illustrates an operation of the medical image analysis apparatus according to an embodiment of this disclosure.

The medical image analysis apparatus (200) can execute a step (310) in which metadata of medical image is predicted using multiple medical images for learning and metadata matched with each of multiple medical images. A prediction model can be acquired by performing machine learning on a relationship between a medical image and metadata based on the data learning unit (110) of the medical image analysis apparatus (200). The prediction model can correspond to the machine learning model in FIG. 1. The medical image analysis apparatus (200) can save the acquired prediction model on the memory or send it to another medical image analysis apparatus (200) via wired or wireless communication.

In addition, the medical image analysis apparatus (200) can execute a step (320) in which metadata of an input medical image is predicted using the learned prediction model. The data recognition unit (120) of the medical image analysis apparatus (200) can predict metadata by applying the prediction model to the input medical image. The prediction model can be acquired from the memory of the medical image analysis apparatus (200) or received from another medical image analysis apparatus (200).

Multiple medical images for learning and the input medical image can be images of various formats.

For instance, multiple medical images for learning and the input medical image can be images that correspond to the DICOM standard. According to the DICOM standard, the medical image analysis apparatus (200) can save information related to medical images on the DICOM header.

The DICOM header can include standard data elements. Standard data elements refer to elements related to medical images defined by the DICOM standard. The medical image analysis apparatus (200) can acquire metadata from standard data elements. The DICOM header can include non-standard data elements. Non-standard data elements are not defined by the DICOM standards, but they refer to elements related to medical images generated by a medical image apparatus manufacturer or medical institution as needed. The medical image analysis apparatus (200) can acquire metadata from non-standard data elements.

Information related to medical images can be saved in storage space other than the DICOM header. The medical image analysis apparatus (200) can save diverse information related to medical images, along with matching relationship of medical images. In addition, the medical image analysis apparatus (200) can acquire metadata based on diverse information related to medical images.

A process of acquiring metadata form the DICOM header is explained in greater detail with FIG. 4 below.

Figure 4:
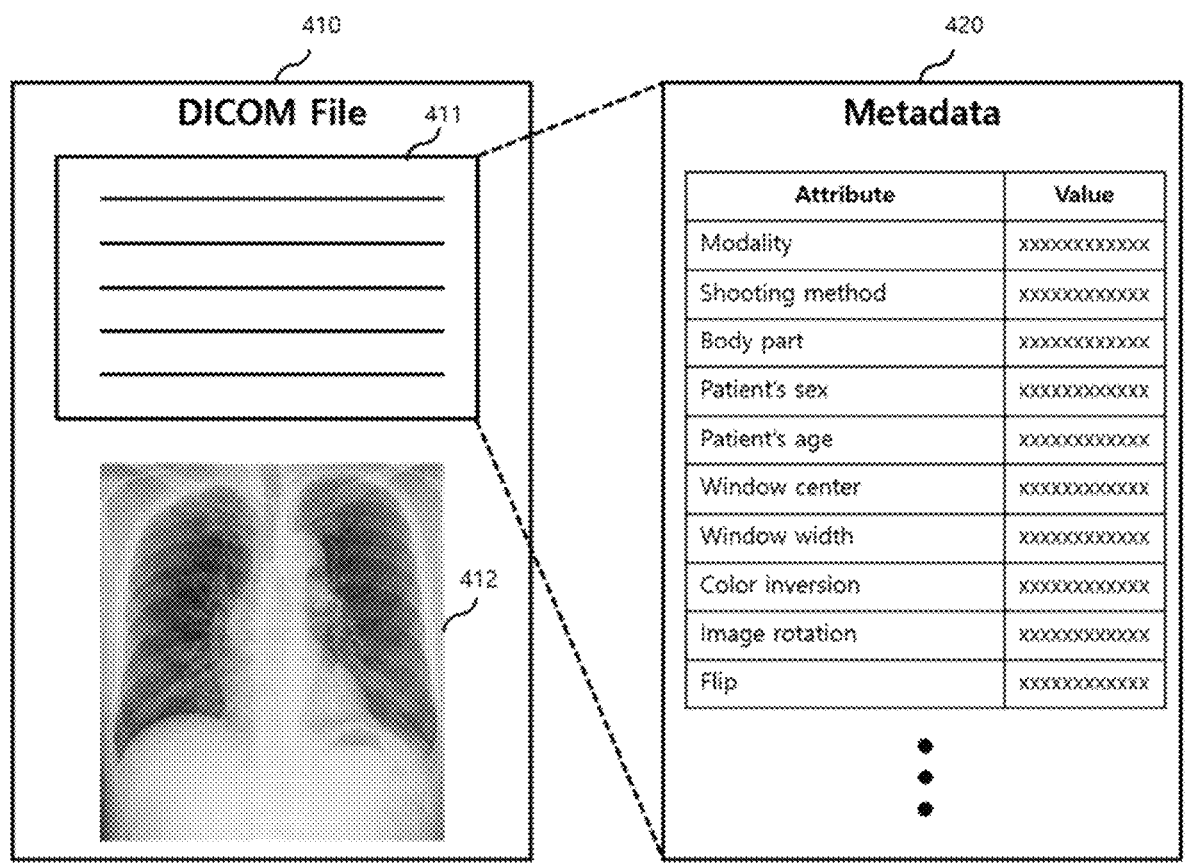
FIG. 4 is a figure that illustrates structure of the DICOM file according to an embodiment of this disclosure.

FIG. 4 is a figure that illustrates a structure of the DICOM file according to an embodiment of this disclosure.

A DICOM file (410) can comprise a DICOM header (411) and a medical image (412). The medical image (412) can include various medical images, for instance at least one of CT, X-RAY, mammography or MRI image. The DICOM header (411) can include diverse information related to medical images. The medical image analysis apparatus (200) can acquire metadata (420) based on diverse information related to the medical image (412) included in the DICOM header (411).

The DICOM header (411) can comprise standard data elements or non-standard data elements. The medical image analysis apparatus (200) can acquire metadata based on standard data elements or non-standard data elements. Metadata (420) can comprise at least one of information related to objects included in a medical image, information about a shooting environment of a medical image, and information related to display method of medical image.

More specifically, information related to objects included in a medical image can include at least one of information about body parts included in the medical image and information about patient. Information about body parts included in the medical image can be expressed as an index that corresponds to body parts. For instance, information about body parts can include at least one of indices indicating the lungs, abdomen, arms or legs.

Information about patients can comprise sex or age information of patients. Age information of patients can be a value that indicates age of the patient as a number. In addition, metadata can comprise the birthday of the patient, and the medical image analysis apparatus (200) can calculate age information of the patient using the birthday of the patient. In addition, age information of the patient can be information that represents an age range, for instance an age group. As an embodiment, age information of the patient can be expressed as an index that indicates child, youth, middle age, old age, or age group.

Information about a shooting environment of medical images can comprise diverse information related to shooting of medical images. The shooting environment information can include at least one of modality information of medical images and information about a shooting method of medical images.

Modality information of medical images can show type of imaging equipment used to shoot medical images. For instance, modality information of medical images can be an index indicating that the medical image (412) is a CT, MRI, X-RAY, mammography, or ultrasonic image. However, modality information of medical images is not limited to these and can show diverse medical images taken on patients.

In addition, information about a shooting environment of medical images can comprise information about a shooting method of medical images. The shooting environment information can correspond to a predefined index that is indicated as a number or text. The shooting environment information can comprise information about whether an X-RAY was irradiated from anterior to posterior of the patient or from posterior to anterior of the patient. In general, an X-RAY is irradiated from posterior to anterior of the patient when the patient is standing up. If the patient has difficulty standing up, an X-RAY is irradiated from anterior to posterior.

Information related to a display method of medical images can comprise at least one of window center information of medical images, window width information, color inversion information, image rotation information, and image flip information.

Figure 5:
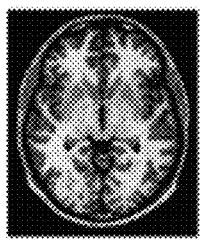
FIG. 5 shows CT information based on window center information and window width information according to an embodiment of this disclosure.

Window center information and window width information are explained with FIG. 5.

FIG. 5 shows CT information based on window center information and window width information according to an embodiment of this disclosure.

Window center information and window width information can be information to adjust brightness and contract of medical images.

A window graph can be drawn based on window center information (531) and window width information (532). Horizontal axis of window graph can represent input pixel values. An input pixel refers to a pixel of an input medical image. Input pixel values can have a minimum value and maximum value. Minimum and maximum values can be determined by at least one of an image shooting device, an image display device, and image encoding and decoding standards. If an input pixel value that has the maximum value can indicate brightest pixel, and an input pixel value that has the minimum value can indicate darkest pixel. However, pixel values are not limited to these indications.

Vertical axis of the window graph can represent output pixel values. The medical image analysis apparatus (200) can determine output pixel values by processing input pixel values. The medical image analysis apparatus (200) can show medical image on display based on output pixel values.

For instance, the window graph (521) can be created if window center information (531) is a and window width information (532) is b. The medical image analysis apparatus (200) can generate a CT image (511) based on window center information (531) and window width information (532). The medical image analysis apparatus (200) can generate the CT image (511) based on window center information (531) or window width information (532) by indicating the input pixel value less than first threshold value as the minimum pixel value and indicating the input pixel value greater than second threshold value as the maximum pixel value. In other words, the medical image analysis apparatus (200) can separately indicate input pixel values that are greater than or equal to the first threshold value and less than or equal to the second threshold value.

The input pixel value less than the first threshold value or the input pixel value greater than the second threshold value can be a clutter signal unimportant for medical image analysis. The medical image analysis apparatus (200) can adjust the first threshold value and second threshold value based on window center information (531) and window width information (532) and only indicate pixels that are important for medical image analysis.

In addition, for instance, the window graph (522) can appear as in FIG. 5 if window center information (531) is a and window width information (532) is c. The medical image analysis apparatus (200) can generate a CT image (512) based on window center information (531) and window width information (532). The medical image analysis apparatus (200) can generate the CT image (511) based on window center information (531) or window width information (532) by separately indicating all input pixel values.

The medical image analysis apparatus (200) can indicate bright part of input pixels to be brighter or darker based on slope of the window graph (522). The medical image analysis apparatus (200) can adjust brightness of the medical image based on window center information (531) or window width information (532). For instance, comparing cases in which window width information (532) is c and window width information (532) is b, the CT image (512) is darker than the CT image (511).

In comparison to the CT image (511), the CT image (512) includes all pixel values and does not lose information. However, since this image expresses all clutter signals that are unimportant for medical image analysis, it may not be optimized for image analysis. The medical image analysis apparatus (200) can optimize the medical image for image analysis by adjusting window center information (531) or window width information (532).

In addition, for instance, the window graph (523) can appear as in FIG. 5 if window center information (531) is d and window width information (532) is c. The medical image analysis apparatus (200) can generate a CT image (513) based on window center information (531) and window width information (532). The medical image analysis apparatus (200) can generate the CT image (513) based on window center information (531) or window width information (532) by processing all input pixel values greater than third threshold value to be bright.

The medical image analysis apparatus (200) can indicate a bright part of input pixels to be brighter or darker using slope of the window graph (522). The medical image analysis apparatus (200) can adjust a brightness of the medical image based on window center information (531) or window width information (532). For instance, comparing cases in which window center information (531) is a and window center information (531) is d, the CT image (512) is darker than the CT image (513).

Input pixel values greater than the third threshold value can be clutter signals that are unimportant for medical image analysis. The medical image analysis apparatus (200) can adjust the third threshold value based on window center information (531) and window width information (532) and only indicate pixels that are important for medical image analysis.

The medical image analysis apparatus (200) can normalize original images that come from diverse environments based on window center information (531) or window width information (532). The preprocessing unit (112) and preprocessing unit (122) of the medical image analysis apparatus (200) can generate a normalized medical image from the original medical image. In addition, the medical image analysis apparatus (200) can provide prediction model to another medical image analysis apparatus. Another medical image analysis apparatus can adjust the medical image based on the prediction model of this disclosure before executing other machine learning cases.

Referring to FIG. 4 again, information related to a display method of medical images can comprise color inversion information. The medical image analysis apparatus (200) can invert color of the medical image based on color inversion information. If color inversion information indicates inversion of color, the medical image analysis apparatus (200) can display the medical image by defining pixel value as value that subtracted the pixel value of the medical image from the maximum pixel value.

The display method information can include image rotation information. Image rotation information can show a size of clockwise or counterclockwise rotation of the medical image taken. Image rotation information can be expressed as an index that corresponds to rotation size or as a number in radian or degree. The medical image analysis apparatus (200) can rotate the medical image based on rotation information of the image.

The display method information can comprise image flip information. Image flip information can represent flipping of the medical image to left and right about vertical axis. However, it is not limited to left and right flip. Image flip information can represent flipping of the medical image up and down about horizontal axis.

Explanation so far was that metadata (420) includes at least one of information related to objects included in medical images, information about shooting information of medical images, and information related to display method of medical images.

As described above, the medical image analysis apparatus (200) can acquire metadata based on information saved on the DICOM header in a standard format. In addition, the medical image analysis apparatus (200) can acquire metadata based on information saved on the DICOM header in a non-standard format. In addition, the medical image analysis apparatus (200) can acquire metadata based on information saved on storage space other than the DICOM header in a non-standard format.

Non-standard formats can differ among medical imaging device manufacturers or hospitals. If metadata is acquired from information saved in a non-standard format, the medical image analysis apparatus (200) can have an inconvenience of having to acquire metadata using different methods for different manufacturers or hospitals providing the medical image.

The medical image analysis apparatus (200) according to this disclosure can generate metadata based on a medical image (412) even if metadata is acquired based on information saved in a non-standard format or there is no information related to the medical image. A step (310) of learning prediction model in FIG. 3 is explained in detail using FIG. 6 and FIG. 7.

Figure 6:
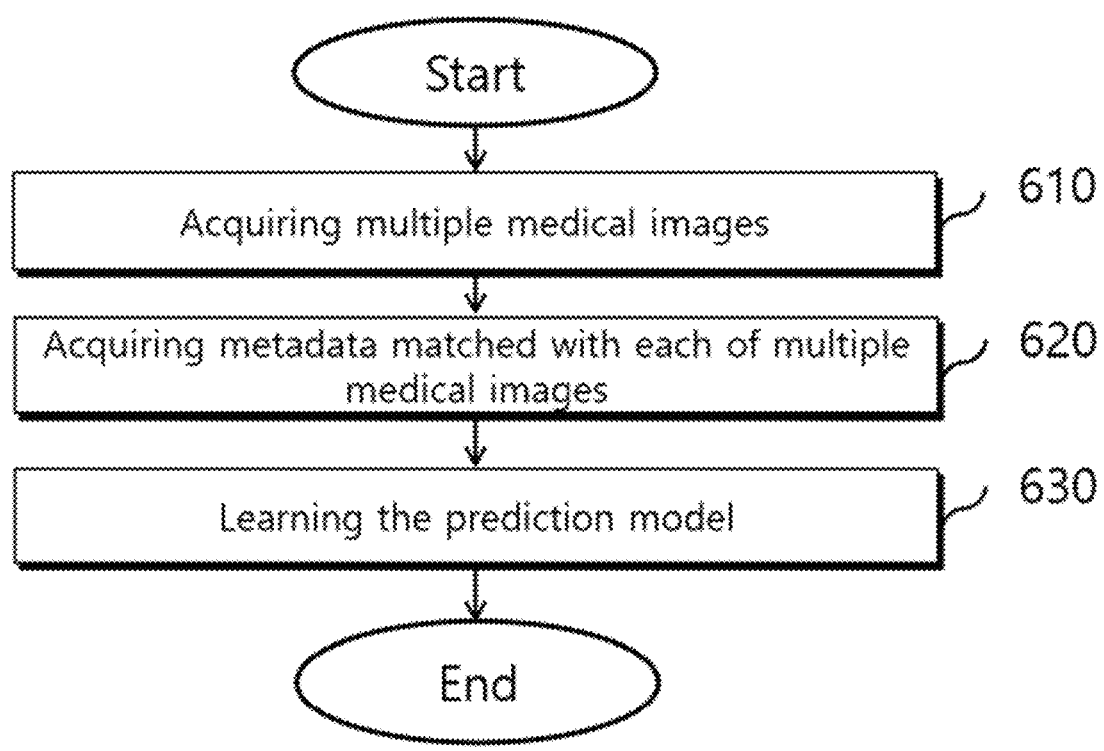
FIG. 6 is a flow diagram that illustrates operation of the medical image analysis apparatus according to an embodiment of this disclosure.
Figure 7:
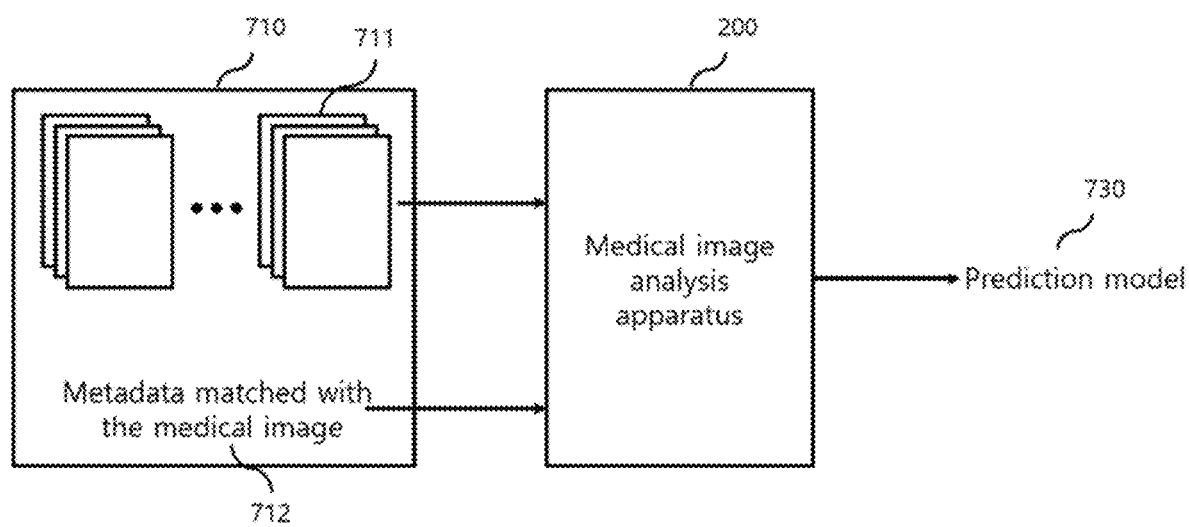
FIG. 7 is a figure that illustrates a prediction model learning process according to an embodiment of this disclosure.

FIG. 6 is a flow diagram that illustrates an operation of the medical image analysis apparatus according to an embodiment of this disclosure. In addition, FIG. 7 is a figure that illustrates a prediction model learning process according to an embodiment of this disclosure.

The medical image analysis apparatus (200) can receive an input data set (710) to learn the prediction model. The input data set (710) can include multiple medical images (711) and metadata (712).

The medical image analysis apparatus (200) can execute a step (610) in which multiple medical images (711) are acquired. For instance, the medical image analysis apparatus (200) can acquire multiple medical images from the memory (220). In addition, the medical image analysis apparatus (200) can acquire multiple medical images based on wired or wireless communication.

The medical image analysis apparatus (200) can execute a step (620) in which metadata (712) matched with each of multiple medical images is acquired. The medical image analysis apparatus (200) can execute a step in which multiple metadata matched with each of multiple medical images are acquired from standard data elements of the DICOM header of each of multiple medical images for learning. However, acquisition is not limited to this. The medical image analysis apparatus (200) can acquire metadata from non-standard data elements of the DICOM header or information of a non-standard format saved on storage space other than the DICOM header. Redundant explanation about this is omitted because it is identical to explanation on FIG. 3 and FIG. 4.

The medical image analysis apparatus (200) can execute a step (630) in which the prediction model is learned using multiple medical images for learning and multiple metadata acquired. The medical image analysis apparatus (200) can perform supervised learning using the original medical image and label data. Label data can be metadata. Label data can be information on the DICOM header, information saved in an area other than the DICOM header, information entered by user, or information about original medical image entered by a medical professional. The medical image analysis apparatus (200) can perform machine learning based on regression or classification according to characteristics of label data.

Machine learning can be used to learn the prediction model of the medical image analysis apparatus (200). Machine learning can be based on neural network. For instance, algorithms such as DNN, RNN, LSTM, BRDNN, and CNN can be used for machine learning, but machine teaming is not limited to them.

The medical image analysis apparatus (200) can output learning result as the prediction model (730). The medical image analysis apparatus (200) can save the prediction model (730) on the memory. The medical image analysis apparatus (200) can send the prediction model (730) to another medical image analysis apparatus (200).

The step (310) of learning the prediction model was explained so far. A step (320) in which metadata is predicted using the prediction model is explained with FIG. 8 and FIG. 9 below.

Figure 8:
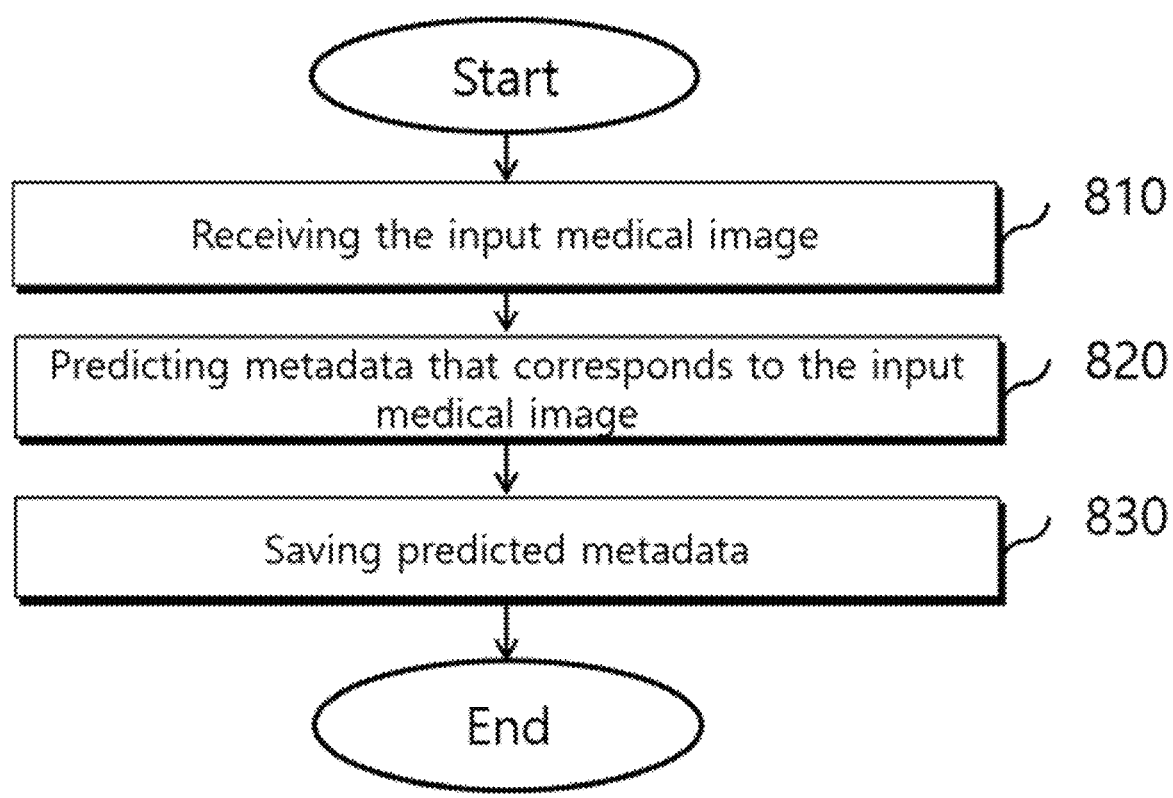
FIG. 8 is a flow diagram that illustrates operation of the medical image analysis apparatus according to an embodiment of this disclosure.
Figure 9:
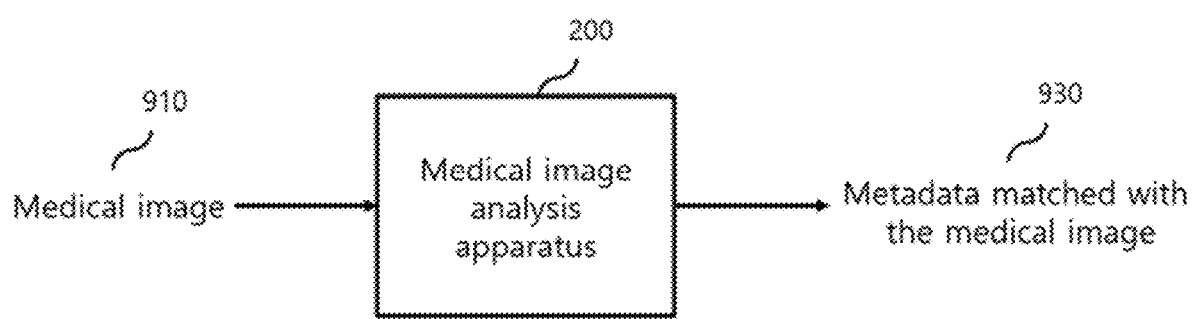
FIG. 9 is a figure that illustrates a process of using the prediction model according to an embodiment of this disclosure.

FIG. 8 is a flow diagram that illustrates an operation of the medical image analysis apparatus according to an embodiment of this disclosure. In addition, FIG. 9 is a figure that illustrates a process of using the prediction model according to an embodiment of this disclosure.

The medical image analysis apparatus (200) can include a prediction model. The medical image analysis apparatus (200) can receive the prediction model from another medical image analysis apparatus (200). In addition, the medical image analysis apparatus (200) can acquire the prediction model by performing machine learning based on multiple medical images and metadata.

The medical image analysis apparatus (200) can execute a step (810) in which a medical image (910) is received. For instance, the medical image analysis apparatus (200) can receive the medical image (910) as user input through an input device. For another instance, the medical image analysis apparatus (200) can receive the medical image (910) from another apparatus via wired or wireless communication. The medical image (910) can be independent from multiple medical images (711). The medical image (910) can be different from or same as multiple medical images (711).

The medical image analysis apparatus (200) can execute a step (820) in which the prediction model is used to predict metadata (930) that corresponds to the input medical image (910). Predicted metadata (930) can comprise at least one of information related to objects included in the medical image (910), information about a shooting environment of the medical image above, and information related to display method of the medical image (910).

As explained earlier, information related to objects included in medical images can include at least one of information about body parts included in medical images and information about the patient. In addition, the shooting environment information can include at least one of modality information of a medical images and information about a shooting method of the medical image. In addition, information related to a display method of medical images can include at least one of window center information of the medical image, window width information, color inversion information, image rotation information, and image flip information.

In addition, the medical image analysis apparatus (200) can execute a step (830) in which metadata (930) predicted for the input medical image (910) is matched with the input medical image (910) and saved. The medical image analysis apparatus (200) can save predicted metadata (930) on the DICOM in a standard format, but it is not limited to the standard format. The medical image analysis apparatus (200) can save predicted metadata (930) on the DICOM header in a non-standard format or save it on storage space other than the DICOM header.

The medical image analysis apparatus (200) can adjust the input medical image to optimal condition or optimal state for target task. For instance, the medical image analysis apparatus (200) can execute an additional step in which the input medical image is adjusted using predicted metadata (930) to detect anomaly in the input medical image. In addition, the medical image analysis apparatus (200) executes a step in which at least one of window center of the input medical image, window width, color, and output direction is adjusted based on predicted metadata (930).

For instance, predicted metadata (930) can comprise at least one of predicted window center information, predicted window width information, predicted color inversion information, predicted image rotation information, and predicted image flip information. The medical image analysis apparatus (200) can adjust window center or window width of the medical image (910) based on predicted window center information or predicted window width information. In addition, the medical image analysis apparatus (200) can adjust color of the medical image (910) based on predicted color inversion information. In addition, the medical image analysis apparatus (200) can decide output direction of the medical image (910) based on predicted image rotation information and predicted image flip information.

The medical image analysis apparatus (200) can predict metadata needed for the original medical image before interpreting lesion from the medical image. In addition, the medical image analysis apparatus (200) can adjust the medical image to be interpretable based on the predicted value. In addition, interpretability of the medical image can be determined based on the predicted value. Therefore, the medical image analysis apparatus (200) can provide a consistent interpretation result without relying on the subjective and variable DICOM header.

Figure 10:
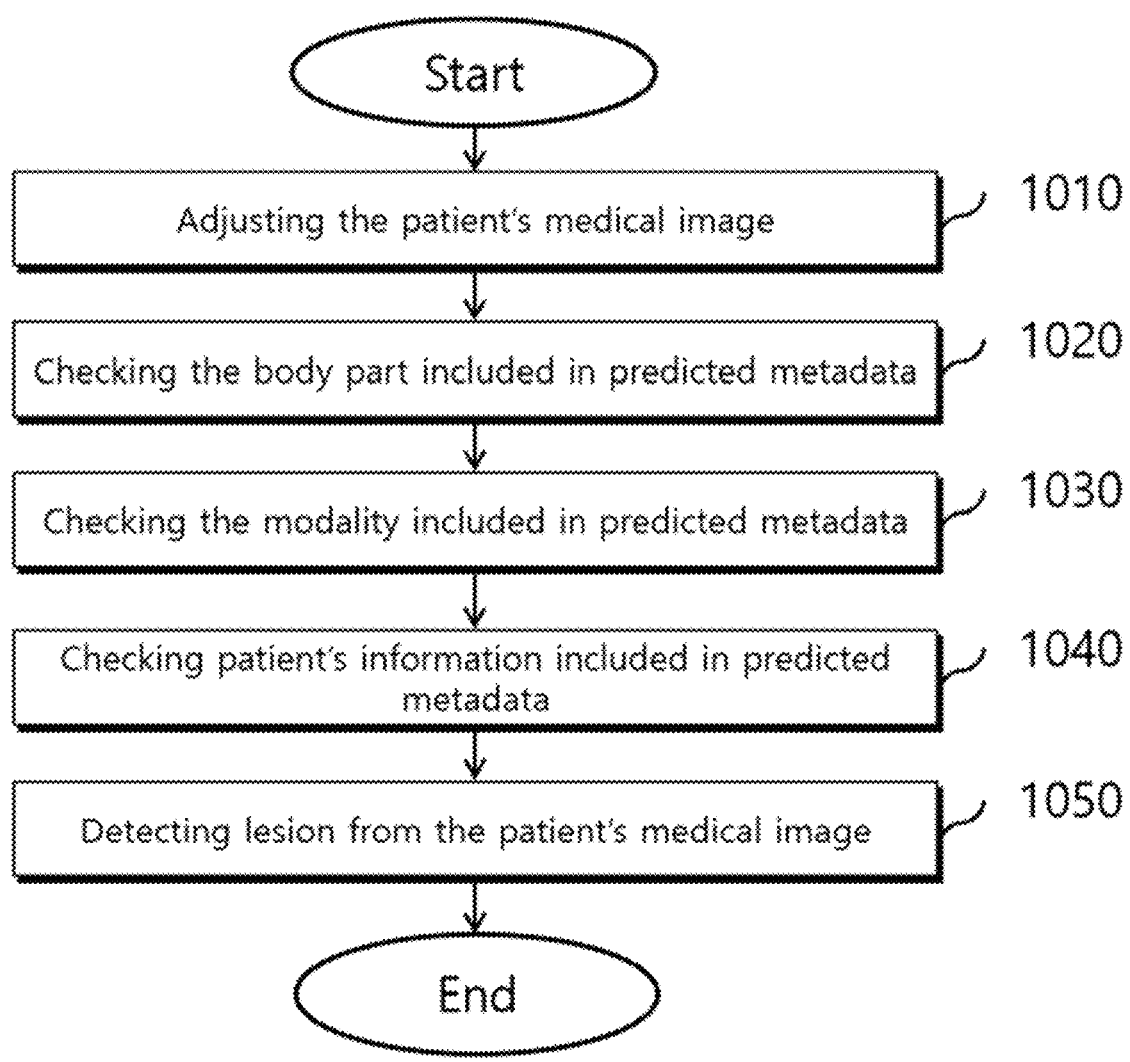
FIG. 10 is a flow diagram that illustrates a process of detecting lesion according to an embodiment of this disclosure.

FIG. 10 is a flow diagram that illustrates process of detecting lesion according to an embodiment of this disclosure.

The medical image analysis apparatus (200) can receive the medical image of the patient. As explained in FIG. 8, the medical image analysis apparatus (200) can predict metadata of the patient's medical image using the prediction model. Since metadata is predicted based on the same prediction model, the medical image analysis apparatus (200) can acquire metadata based on the same criteria regardless of the medical image received. Therefore, the medical image analysis apparatus (200) can increase the success rate of the target task by applying machine learning to the medical image and metadata. The target task can be detection of lesion.

The medical image analysis apparatus (200) can execute a step (1010) in which the patient's medical image is adjusted based on predicted metadata to detect anomaly in the input medical image. In addition, the medical image analysis apparatus (200) can execute a step in which at least one of window center of the input medical image, window width, color, and output direction is adjusted.

The medical image analysis apparatus (200) can execute a step (1020) in which body parts included in predicted metadata are checked. The medical image analysis apparatus (200) can verify whether body part information of predicted metadata agrees with the body part for which abnormality (anomaly) is to be detected.

For instance, the user may need a medical image for a specific body part to diagnose abnormality using the medical image of the patient. The user can enter information about the specific body part into the medical image analysis apparatus (200). Otherwise, the medical image analysis apparatus (200) can automatically acquire information about the specific body part that corresponds to lesion that the user is looking for. The medical image analysis apparatus (200) can verify whether the patient's medical image corresponds to the specific body part by comparing information about the specific body part with body part information included in metadata. If information about the specific body part does not agree with body part information included in metadata, the medical image analysis apparatus (200) can acquire a new medical image of the patient or execute operation to acquire a new medical image of the patient.

The medical image analysis apparatus (200) can executed a step (1030) in which modality included in predicted metadata is checked. The medical image analysis apparatus (200) can verify whether modality information of predicted metadata is appropriate for detecting anomaly.

For instance, the user may need a medical image of a specific modality to diagnose abnormality using the medical image of the patient. The user can enter information about the specific modality into the medical image analysis apparatus (200). Otherwise, the medical image analysis apparatus (200) can automatically acquire information about the specific modality to detect lesion that the user is looking for. The medical image analysis apparatus (200) can verify whether the patient's medical image is based on the specific modality by comparing information about the specific modality with modality information included in metadata. If information about the specific modality does not agree with modality information included in metadata, the medical image analysis apparatus (200) can acquire a new medical image of the patient or execute operation to acquire a new medical image of the patient.

The medical image analysis apparatus (200) can executed a step (1440) in which patient information included in predicted metadata is checked. The medical image analysis apparatus (200) can verify whether patient information of predicted metadata is appropriate for detecting abnormality.

For instance, the user may need information about a specific patient to diagnose abnormality using the medical image of the patient. The medical image analysis apparatus (200) can decide whether the target of diagnosis is the same person as the patient of the medical image. In addition, the medical image analysis apparatus (200) can diagnose the patient of specific age range to diagnose abnormality. For instance, the user can enter patient information into the medical image analysis apparatus (200). Otherwise, the medical image analysis apparatus (200) can automatically acquire patient information to detect lesion that the user is looking for. The medical image analysis apparatus (200) can compare input patient information with patient information included in metadata. If input patient information does not agree with patient information included in metadata, the medical image analysis apparatus (200) can display a warning message.

The medical image analysis apparatus (200) can execute a step (1050) in which lesion is detected from the medical image of the patient. The medical image analysis apparatus (200) can use a machine learning model specialized in lesion detection to detect lesion from the medical image.

Various embodiments were examined so far. A person with common knowledge in the technical field of this invention would understand that this invention can be embodied into various other forms without deviating from essential characteristics of this invention. Therefore, the embodiments disclosed must be considered from an explanatory perspective instead of a limited perspective. Scope of this invention is shown in claims instead of earlier explanation, and all differences within this scope should be interpreted as to be included in this invention.

On the one hand, certain embodiments of this invention described above can be written as programs that can be executed on a PC, and they can be embodied on a general-purpose digital PC that operates the programs above using computer readable recording media. Computer readable recording media above include storage media such as magnetic storage media (for instance, ROM, floppy disk, hard disk, etc.) and optical reading media (for instance, CD-ROM, DVD, etc.).

What is claimed is:

1. A computerized medical image analysis method, using a hardware processor and a hardware memory, comprising:
   machine-training, at a medical image analysis device comprising the hardware processor, a prediction model for predicting metadata of an input medical image, wherein the machine-training of the prediction model is based on a plurality of image-metadata sets each comprising a training medical image and metatdata of the training medical image;
   processing, at the medical image analysis device and using the machine-trained prediction model, the input medical image to obtain predicted metadata of the input medical image, wherein the predicted metadata comprises at least one of information related to one or more objects included in the input medical image, information about a shooting environment of the input medical image, and information related to a display method of the input medical image;
   adjusting, at the medical image analysis device, the input medical image using the predicted metadata; and
   processing, at the medical image analysis device, the adjusted input medical image to locate a lesion contained in the adjusted input medical image,
   wherein the plurality of image-metadata sets comprise a plurality of digital imaging and communications in medicine (DICOM) files each comprising a DICOM image file and a DICOM header,
   wherein the input medical image is obtained from an input DICOM file comprising an input DICOM header of the input medical image, and
   wherein the adjusting of the input medical image is performed using the predicted metadata without relying on at least one of a plurality of elements of the input DICOM header.

2. The method of claim 1, wherein the information related to one or more objects included in the input medical image comprises at least one of information about one or more body parts included in the input medical image and information about a patient of the input medical image,
   wherein the shooting environment information comprises at least one of modality information of the input medical image and information about a shooting method of the input medical image, and
   wherein the display method information comprises at least one of window center information, window width information, color inversion information, image rotation information, and image flip information of the input medical image.

3. The method of claim 2, further comprising adjusting a brightness or contrast of the input medical image based on at least one of the window center information and the window width information.

4. The method of claim 2, wherein the window width information represents a difference between a minimum pixel value and a maximum pixel value of the input medical image.

5. The method of claim 2, wherein the window center information represents at least one of a first threshold value of the input medical image greater than a minimum pixel value, or a second threshold value of the input medical image less than a maximum pixel value.

6. The method of claim 1, further comprising matching and saving the predicted metadata of the input medical image in association with the input medical image.

7. The method of claim 6, wherein the predicted metadata is saved on the input DICOM header of the input medical image.

8. The method of claim 1, wherein adjusting the input medical image comprises,
   adjusting at least one of a window center, a window width, a color, and an output direction of the input medical image based on the predicted metadata.

9. The method of claim 1, wherein the at least one of the plurality of elements of the input DICOM header corresponds to the predicted metadata.

10. The method of claim 1, further comprising:
    verifying, at the medical image analysis device, whether body part information of the predicted metadata matches a target body part for which abnormality is to be detected;

verifying, at the medical image analysis device, whether modality information of the predicted metadata is appropriate for detecting anomaly; and verifying, at the medical image analysis device, whether patient information of predicted metadata is appropriate for detecting abnormality.

11. A medical image analysis apparatus comprising a memory storing computer-executable instructions and a processor configured to execute the computer-executable instructions, wherein the processor is configured, by executing the computer-executable instructions, to perform:

machine-training a prediction model for predicting metadata of an input medical image based on a plurality of image-metadata sets each comprising a training medical image and metadata of the training medical image;

processing, using the machine-trained prediction model, the input medical image to obtain predicted metadata of the input medical image, wherein the predicted metadata comprises at least one of information related to one or more objects included in the input medical image, information about a shooting environment of the input medical image, and information related to a display method of the input medical image;

adjusting the input medical image using the predicted metadata; and processing the adjusted input medical image to locate a lesion contained in the adjusted input medical image, wherein the plurality of image-metadata sets comprise a plurality of digital imaging and communications in medicine (DICOM) files each comprising a DICOM image file and a DICOM header, wherein the input medical image is obtained from an input DICOM file comprising an input DICOM header of the input medical image, and wherein the adjusting of the input medical image is performed using the predicted metadata without relying on at least one of a plurality of elements of the input DICOM header.

12. The apparatus of claim 11, wherein the information related to the one or more objects included in the input medical images comprises at least one of information about one or more body parts included in the input medical image and information about a patient of the input medical image, wherein the shooting environment comprises at least one of modality information of the input medical image and information about a shooting method of the input medical image, and wherein the display method information comprises at least one of window center information, window width information, color inversion information, image rotation information, and image flip information of the input medical image.

13. The apparatus of claim 12, wherein the processor is further configured to adjust a brightness or contrast of the input medical image based on at least one of the window center information and the window width information.

14. The apparatus of claim 12, wherein the window width represents a difference between a minimum pixel value and a maximum pixel value of the input medical image.

15. The apparatus of claim 12, wherein the window center represents at least one of a first threshold value of the input medical image greater than a minimum pixel value, or a second threshold value of the input medical image less than a maximum pixel value.

16. The apparatus of claim 11, wherein the processor is further configured, by executing the computer-executable instructions, to perform matching and saving the predicted metadata of the input medical image with the input medical image.

17. The apparatus of claim 16, wherein the processor is further configured, by executing the computer-executable instructions, to perform saving the predicted metadata on the input DICOM header of the input medical image.

18. The apparatus of claim 11, wherein the processor is further configured, by executing the computer-executable instructions, to perform adjusting at least one of a window center, a window width, a color, and an output direction of the input medical image based on the predicted metadata.

19. The apparatus of claim 11, wherein the at least one of the plurality of elements of the input DICOM header corresponds to the predicted metadata.

20. The apparatus of claim 11, wherein the processor is further configured to:

verify whether body part information of the predicted metadata matches a target body part for which abnormality is to be detected;

verify whether modality information of the predicted metadata is appropriate for detecting anomaly; and verify whether patient information of predicted metadata is appropriate for detecting abnormality.

* * * * *

UNITED STATES PATENT AND TRADEMARK OFFICE
CERTIFICATE OF CORRECTION

PATENT NO.         : 10,824,908 B1
APPLICATION NO.    : 16/708205
DATED              : November 3, 2020
INVENTOR(S)        : Jongchan Park and Donggeun Yoo Page 1 of 1

It is certified that error appears in the above-identified patent and that said Letters Patent is hereby corrected as shown below:

On the Title Page

On page 2, In the right column, item (56) Other Publications, at Line 13, change "Alloance" to --Allowance--.

In the Specification

In Column 1 at Line 50, delete "*teaming*" and insert --*learning*--.

In Column 7 at Line 13, delete "*teaming*" and insert --*learning*--.

In Column 7 at Line 27, delete "*teamed,*" and insert --*learned,*--.

In Column 7 at Line 44, delete "*teaming*" and insert --*learning*--.

In Column 14 at Line 40, delete "*teaming*" and insert --*learning*--.

In the Claims

In Column 17 at Line 60, Claim 1, change "metatdata" to --metadata--.

Signed and Sealed this
Second Day of March, 2021

Drew Hirshfeld
*Performing the Functions and Duties of the
Under Secretary of Commerce for Intellectual Property and
Director of the United States Patent and Trademark Office*